United States Patent
Suzuki et al.

(10) Patent No.: US 8,228,489 B2
(45) Date of Patent: Jul. 24, 2012

(54) OPTICAL SENSING SYSTEM FOR LIQUID FUELS

(75) Inventors: Carlos Kenichi Suzuki, Campinas (BR); Edmilton Gusken, Bauru (BR); Allan Caro Mercado, Campinas (BR); Eric Fujiwara, São Paulo (BR); Eduardo Ono, Distrito de Barão Geraldo (BR)

(73) Assignee: Universidade Estadual de Campinas—Unicamp, Campinas—SP (BR)

( * ) Notice: Subject to any disclaimer, the term of this patent is extended or adjusted under 35 U.S.C. 154(b) by 267 days.

(21) Appl. No.: 12/672,202

(22) PCT Filed: Aug. 6, 2008

(86) PCT No.: PCT/BR2008/000231
§ 371 (c)(1),
(2), (4) Date: Feb. 25, 2010

(87) PCT Pub. No.: WO2009/018638
PCT Pub. Date: Feb. 12, 2009

(65) Prior Publication Data
US 2010/0208243 A1   Aug. 19, 2010

(30) Foreign Application Priority Data
Aug. 6, 2007  (BR) ...................................... 0703260

(51) Int. Cl.
*G01N 21/41* (2006.01)
(52) U.S. Cl. ........... 356/128; 356/436; 73/592; 250/343
(58) Field of Classification Search .......... 356/128–137, 356/432–440; 250/343; 73/592, 299, 301
See application file for complete search history.

(56) References Cited

U.S. PATENT DOCUMENTS

| | | | |
|---|---|---|---|
| 5,157,452 A * | 10/1992 | Suzuki et al. ................. | 356/128 |
| 5,237,983 A * | 8/1993 | Willey et al. .................. | 123/688 |
| 5,534,708 A * | 7/1996 | Ellinger et al. ............... | 250/577 |
| 5,828,452 A * | 10/1998 | Gillispie et al. .............. | 356/328 |
| 6,341,629 B1 * | 1/2002 | Clark et al. .................... | 141/83 |
| 2009/0076744 A1 * | 3/2009 | Anderson ....................... | 702/55 |

\* cited by examiner

*Primary Examiner* — Hoa Pham
(74) *Attorney, Agent, or Firm* — The Nath Law Group; Jerald L. Meyer; Stanley N. Protigal

(57) ABSTRACT

The present invention relates to a thermally compensated optical sensing system for identifying various types of liquid fuels and/or the ratio in liquid fuel mixtures on real time. In this system, an optical fiber is used as a light guide and a sensor device for determining the refractive index of liquid fuels through the principle of reflectivity. Starting from a light source, light is transmitted interiorly of the optical fiber to the test probe which is in contact with the fuel. The optical signal resulting from the interaction between light and fuel is a function of refractive indexes of the optical fiber and the fuel, the wavelength of light used, and the fuel temperature. The system proposed herein relates to the use of this optical system in liquid fuels by using optical fibers having suitable refractive indexes as a function of the fuel type and/or fuel mixture being analyzed, allowing the sensitivity of the optical system to be optimized according to application requirements.

6 Claims, 4 Drawing Sheets

OPTICAL SENSING SYSTEM FOR LIQUID FUELS

TECHNICAL FIELD

The present invention refers to a device and an optical sensing process for identifying liquid fuels and/or determining the ratio in liquid fuel mixtures in real time, comprising a thermally-compensated optical system and an optical fiber acting as a sensor device. This invention uses optical components which act on the light-fuel interaction, allowing the refractive index of the liquid to be accurately determined through Fresnel's principle, enabling its correlation with the type of fuel and/or with the concentration in a fuel mixture through calibration curves.

The system proposed herein uses an optical fiber which transmits light internally to the test probe which is in contact with the fuel. The optical signal originating from the interaction between light and fuel is collected by an optical detector, making it possible to identify the type of fuel in real time and/or determine the ratio in fuel mixtures in its entire concentration range. Such optical signal resulting from the interaction of light in the fiber-fuel interface is a function of refractive indexes of the optical fiber and the fuel, the wavelength of light used, and the fuel temperature. The system proposed herein relates to the use of this optical system in liquid fuels by using optical fibers having suitable refractive indexes as a function of the fuel and/or fuel mixture being analyzed, allowing the sensitivity of the optical system to be optimized according to requirements of the application.

In the current world scenario, a growing trend can be seen towards the use of alternative and renewable energy sources to replace or work in conjunction with fossil fuels (oil byproducts, coal, among others). In this context, the development of fuel sensing devices has become essential in order to determine the various existing types of fuels, as well as its concentrations in fuel mixtures. An exemplary application for the sensing device, directed towards fuel quality control, is the use in fuel production, distribution and storage systems, allowing the product to be classified and compared against a quality standard. Besides these applications, sensors are also employed to detect the ratio of different fuels in a mixture, what is particularly useful to the operation of the combustion system in dual-fuel engines. On the other hand, such sensor could also aid in detecting possible frauds (fuel adulteration) such as, for example, the addition of water into ethanol, ethanol into gasoline, solvents into gasoline, and vegetable oil or ethanol into diesel.

BACKGROUND OF THE INVENTION

Devices and methods for fuel detection have been used increasingly often. U.S. Pat. No. 5,958,780 discloses a method of identifying liquids, such as gasoline or other oil byproducts, by introducing miscible markers into these liquids, and subsequently identifying the same by analyzing the concentration of the marker through absorption spectrometry. The presence and concentration of these markers would indicate the addition or absence of solvents. Patent PI 0406097-0 A proposes measuring the anhydrous ethyl alcohol fuel (AEAF) concentration by means of the electrical conductivity or resistivity of the fuel itself. Patent PI 8405986 proposes measuring the fuel concentration by measuring the dielectric constant of the mixture. Apparatuses and processes based on optical fiber sensors for liquid detection have been frequently conceived. Patent PI 3058301 A discloses an optical system for detecting and identifying liquids through the principle of reflectivity, while patent PI-5040213 A uses the same method for detecting and/or identifying leakages in fuel and beverage tanks. Patent PI 8702079 A proposes a method for detecting the ratio of the gasoline-ethanol mixture by measuring the critical angle of an incident beam of an optical system. Patent PI 8803374 A proposes a thermally-compensated method for detecting the gasoline-ethanol mixture ratio through an optical system which determines the refractive index of the fuel mixture. Patent PI 9200613 A proposes a thermally-compensated system for precisely detecting the mixture between two types of liquid fuels by measuring the refractive index of the fuel mixture using an optical prism.

However, existing sensors for detection or identification of liquids lack some important features and functionalities in terms of liquid fuels. For example, U.S. Pat. No. 5,958,780 determines the addition of special markers to the fuel and other components, such as to make its subsequent identification or concentration measurement possible by means of analysis in specialized laboratories and equipments. In the case of procedures mentioned in patents PI 0406097-0 A and PI 8405986 A, the latter employ the method of introducing electrical currents through fuels in order to determine the electrical conductivity or resistivity property, which may cause serious explosion hazards.

With regard to the identification of liquid fuel mixtures, such as adulterated fuels, or ethanol-gasoline flex-fuel automotive fuel mixture systems, or even the diesel-biodiesel mixture, there is a need for using highly-sensitive systems and sensor optical fibers. For example, systems disclosed in patents PI 305830-1 A and PI 504021-3 A, which were devised for detection and identification of leakages in fuel and beverage storage tanks, lack a higher sensitivity, due to limitations of the sensor fiber itself. Patent PI 8702079 A does not present a simple system for use in motor vehicles, and also assumes its use only in determining the ethanol-gasoline mixture ratio, without embracing mixtures between other types of fuel. The system proposed in patent PI 8803374 A requires three amplifiers to compensate for temperature variations. Lastly, patent PI-9200613 A uses an optical prism for determining the refractive index, as well as a bulky and complicated apparatus for supporting and coupling the same in motor vehicles.

SUMMARY OF THE INVENTION

In order to solve the problems above, the present invention provides an optical sensing device and system for identifying liquid fuels and/or determining the concentration of fuels in liquid fuel mixtures in real time using a compact, high-precision apparatus which does not pose any explosion hazard. The approach of the present invention has as its basis two principles: (i) principle of light guiding and (ii) principle of optical reflectivity (Fresnel's Principle). Light is guided internally of an optical fiber, from the light source to the test probe, wherein the optical reflectivity phenomenon (Fresnel's principle of reflection) occurs at the fiber-fuel interface, from which light is reflected back to the optical fiber, as shown in FIG. 1 of the drawings. The intensity of the reflected light obtained by the optical detector is a function of the refractive indexes both from the optical fiber and the fuel, the wavelength of light used, and the fuel temperature. The refractive index of fuel mixtures, such as ethanol and gasoline, which are miscible with each other, varies according to the ratio of these fuels in the mixture. Thus, by measuring the intensity of the light returning to the detector, it is possible to determine the type and concentration of fuels with a simple assembly which allows exact measurements (thanks to the size of the sensor) and real-time readings. However, some fuels such as diesel and biodiesel have refractive indexes which are near those of standard optical fibers (n≈1.465), which greatly reduces the sensing sensitivity and renders unfeasible the use of these fibers in sensing these types of fuels. This problem is still exacerbated when it becomes necessary to determine the ratio in mixtures which involve these fuels, for example, biodiesel-diesel and ethanol-diesel mixtures. In order to optimize the identification and determination of the concentration of different types of fuels and mixtures, the use of special optical fibers having refractive indexes which are more suitable for sensing of said fuels is provided.

Accordingly, the present invention may be employed, for example, in ethanol production plants for controlling the water concentration in the produced ethanol and controlling the fuel quality. The portability of this system also allows to check for possible fuel adulterations during the whole production, transportation, and distribution cycle, by being installed in fuel distribution facilities, tank trucks, gas stations, and the motor vehicles themselves.

BRIEF DESCRIPTION OF THE DRAWINGS

The invention will be described in the following with reference to its typical embodiments and with further reference to the annexed drawings, in which.

DETAILED DESCRIPTION OF THE INVENTION

Figure 1:
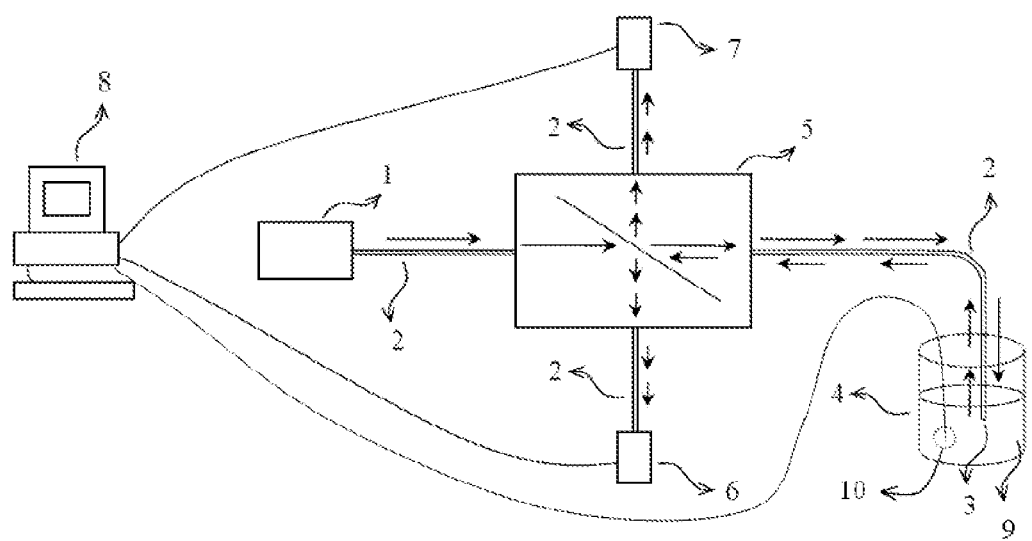
FIG. 1 shows a simplified model of the optical sensing system for liquid fuels, being comprised of a light source (1), optical fibers (2), a test probe (3), a fuel container (4), a splitter (5), a photodetector for the signal from the photonic sensor (6), optionally a photodetector for the reference signal from the light source (7), a storage, processing and data presentation unit (8), a fuel (9), and a temperature sensor (10).

The optical sensing system consists of a light source (1) to which a splitter (5) is coupled, wherein a part of the light beam from the light source (1) is optionally directed to a detector (7) which will occasionally serve as a reference, and other part of the beam is directed to the test probe (3) which will be immersed in the liquid fuel. Part of the light coming from the test probe is reflected at the fiber-fuel interface, returning back to the detector (6) through the splitter (5). The signal arriving at the detector (6) is converted and optionally compared with the signal from the reference detector (7), and is sent to a processing unit (8), which may be a microprocessor, correlating the signal from the detector with the type of fuel and/or determining the ratio in fuel mixtures through calibration curves previously input into the system. The fuel temperature is determined by means of a sensor (10) for correcting the thermal effect. A simplified model of the apparatus is shown in FIG. 1 of the drawings.

Figure 2:
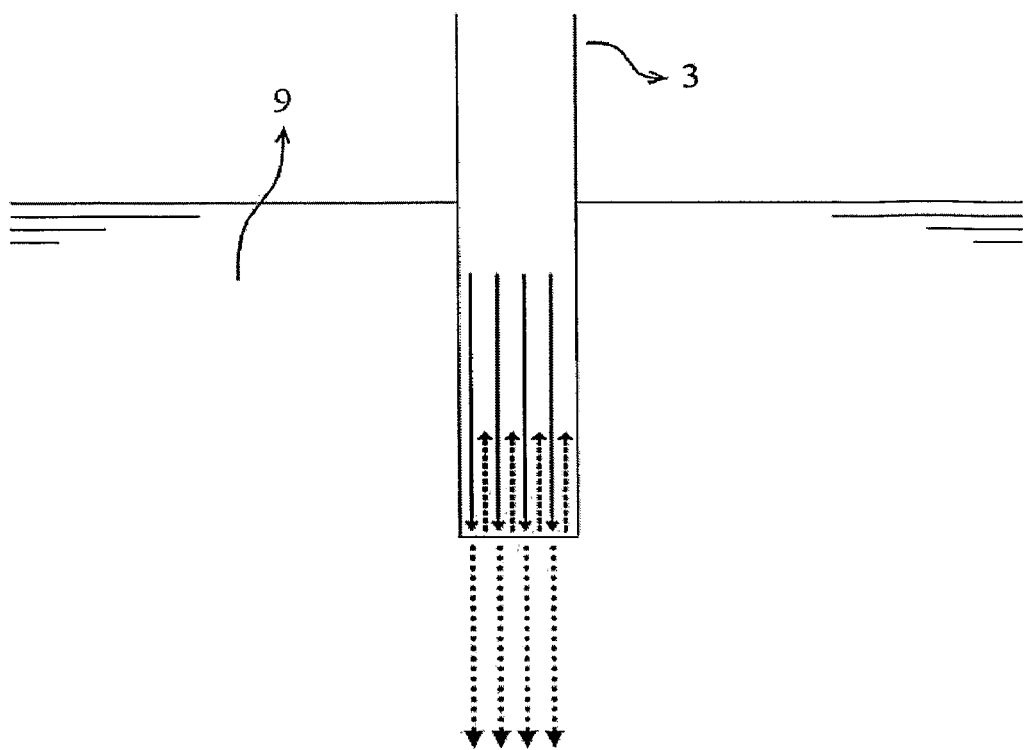
FIG. 2 shows a simplified scheme of the principle of light reflectivity acting on the interface between the test probe (3) and the fuel (9).
Figure 3:
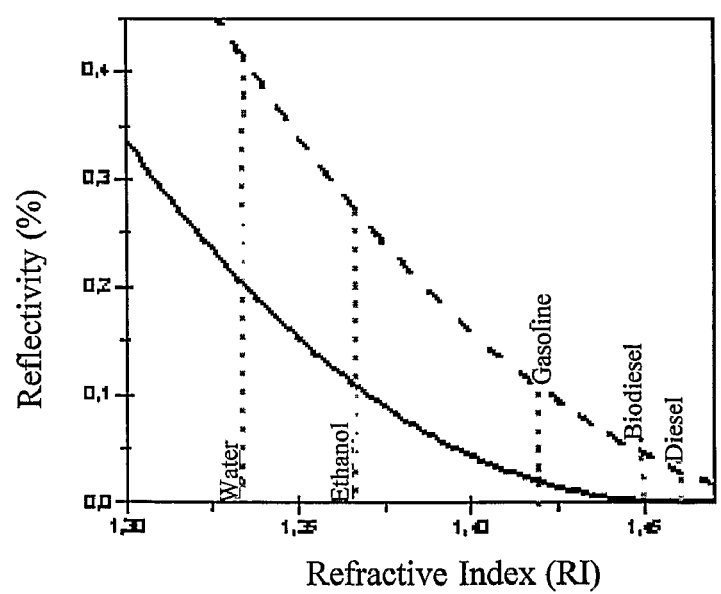
FIG. 3 shows an example of two types of sensors: an optical fiber with a standard refractive index $n_1$=1.465 (solid line curve) and a special optical fiber with a refractive index $n_1'$=1.520 (dashed line curve), and the effect on reflectivity for different types of fuel.

In the system proposed herein, the fiber-fuel interface is composed of two distinct media: a medium 1, constituted by the material which makes up the optical fiber, and a medium 2, constituted by the liquid fuel. At this interface, the light coming from the light source is not fully transmitted from the optical fiber to the fuel, being partially reflected back to the detector. The principle of reflectivity (Fresnel's principle) acting on the interface area between the test probe (3) and the liquid fuel (9) determines which light fraction is reflected on the interface, as shown in FIG. 2 of the drawings. Fresnel's principle can be analytically described through the following equations:

$$R_s = \left[\frac{sen(\theta_r - \theta_i)}{sen(\theta_r + \theta_i)}\right]^2 = \left[\frac{n_1\cos(\theta_i) - n_2\cos(\theta_r)}{n_1\cos(\theta_i) + n_2\cos(\theta_r)}\right]^2,$$

$$R_p = \left[\frac{tg(\theta_r - \theta_i)}{tg(\theta_r + \theta_i)}\right]^2 = \left[\frac{n_1\cos(\theta_r) - n_2\cos(\theta_i)}{n_1\cos(\theta_r) + n_2\cos(\theta_i)}\right]^2,$$

$$R = (R_s + R_p)/2.$$

where:
R represents the reflectivity between media 1 and 2;
$R_s$ and $R_p$ represent the effect of reflectivity on polarized light;
$n_1$ represents the refractive index of medium 1 (test probe);
$n_2$ represents the refractive index of medium 2 (fuel liquid);
$\theta_i$ represents the angle between the incident light beam and the normal of the interface of media 1 and 2;
$\theta_r$ represents the angle between the refracted light beam and the normal of the interface of media 1 and 2;

Most commonly-used liquid fuels have distinct and well-defined refractive indexes, which allows them to be identified through refractometry. Considering medium 1 as the material which makes up the sensor optical fiber, having a refractive index, for example, near to 1.465 (a typical value for standard optical fibers), and medium 2 as the liquid fuel, it becomes possible to determine the liquid fuel refractive index through the reflectivity equation shown above. With the system having been supplied with refractive indexes of various types of fuel, the processing unit is able to identify the type of fuel by directly comparing the measured and stored refractive indexes. However, devices which use optical sensors generally are not optimized for liquid fuel sensing, and thus do not provide the accuracy required in specific cases. One such case concerns the difficulty the system has in distinguishing between fuels as they have refractive indexes which are very near to the refractive index of standard optical fibers (n≈1.465). An optical system using a standard optical fiber does not have enough accuracy to differentiate, for example, diesel from biodiesel. As shown in the graph of FIG. 3, this accuracy can be increased by using a special fiber having a higher refractive index (n≈1.520), thereby allowing the fuel to be properly identified. As a reference, refractive indexes of commonly-used fuels, as well as of other liquids used in fuel mixtures are listed in Table 1.

TABLE 1

Refractive indexes at 20° C. and
λ = 589 nm

| Liquid | Refractive Index |
| --- | --- |
| Methanol | 1.329 |
| Water | 1.333 |
| Anhydrous ethyl alcohol | 1.362 |
| Ethanol | 1.377 |
| Gasoline (C-Type) | 1.409 |
| Gasoline (A-Type) | 1.420 |
| Kerosene | 1.448 |
| Biodiesel | 1.450 |
| Diesel | 1.460 |

An exemplary application is in the identification of adulterated fuels. The addition of liquids into the compliant (unadulterated) fuel changes the properties of the original fuel and, consequently, the refractive index of the resulting mixture, allowing adulteration to be detected through the system proposed herein. Accordingly, the higher the difference between refractive indexes of the compliant fuel and the analyzed fuel, the higher is the adulteration degree.

Figure 4:
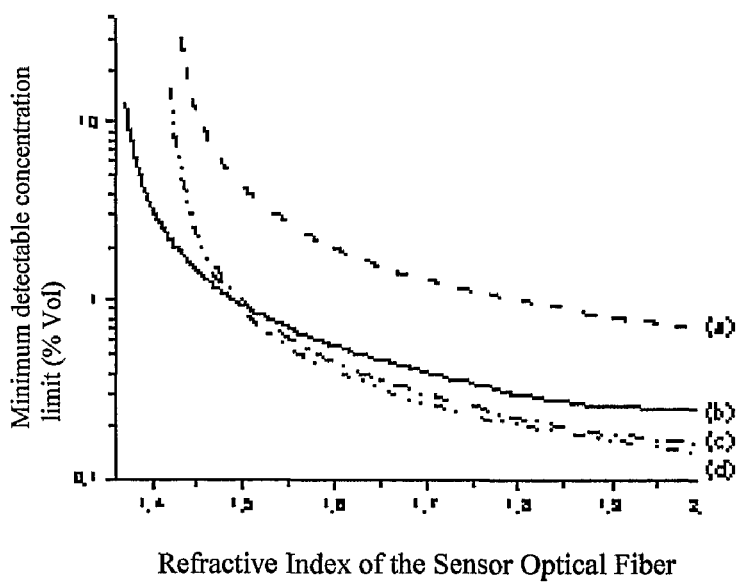
FIG. 4 shows the effect the refractive index of the optical fiber has on the sensitivity of the optical system for a water-ethanol mixture represented by a solid line curve (b), wherein curve (a) represents a thinner-gasoline mixture, curve (c) represents a turpentine-gasoline mixture, and curve (d) represents an ethanol-gasoline mixture.

A common way by which fuel is adulterated is by adding water into ethanol. In that case, the different types of ethanol used as a fuel should be taken into account. Hydrated ethyl alcohol fuel (HEAF), commonly known as hydrated ethanol, comprises from about 4% to 7% water in its composition, but is still a compliant fuel. HEAF has a slightly higher refractive index than anhydrous ethyl alcohol fuel (AEAF), commonly known as anhydrous ethanol, which has a minimum amount of water in its composition. As shown in FIG. 4, an optical system using an optical fiber having a standard refractive index establishes a minimum detectable concentration of water in ethanol of about 1%. Concentrations up to 0.5% water, for example, may be detectable by using special optical fibers having refractive indexes higher than 1.65.

Another common way by which fuel is adulterated is by adding ethanol or solvents into gasoline. As is shown in FIG. 4 in the drawings, the optical sensing using a standard fiber (n≈1.465) establishes the minimum ethanol detection in the ethanol-gasoline mixture for concentrations above 2% by volume and only 5% for solvents, such as the thinner in the thinner-gasoline mixture. For lower concentrations, adulteration can only be detected by increasing the sensitivity of the system, which can be achieved through the use of special optical fibers having a higher refractive index.

The refractive index of a liquid fuel mixture, miscible with each other, is determined by the mean refractive index of fuels making up the mixture, weighted by its respective volumetric ratios. By knowing a priori that two distinct types of fuel make up a binary mixture, one can determine the ratio between these fuels through this relationship:

$$n_{mix} = n_1 \times C_1 + n_2 \times C_2, \text{ where } C_1 + C_2 = 1,$$

which provides:

$$C_1 = \frac{n_{mix} - n_2}{n_1 - n_2}$$

where:
$n_{mix}$ represents the refractive index of the mixture;
$n_1$ and $n_2$ represent the refractive indexes of fuels 1 and 2, respectively;
$C_1$ and $C_2$ represent ratios of fuels 1 and 2, respectively.

An example application could be in the determination of the ratio of fuel mixtures used in dual-fuel (flex-fuel) motor engines, such as the ethanol-gasoline mixture. The variation in the ratio of each fuel is reflected on the refractive index of the fuel mixture.

The present invention also contemplates the combined use of various sensors of the system proposed herein. In the case of dual-fuel (flex-fuel) motor vehicles, for example, it is desirable to provide two independent sensors acting in conjunction. One of the sensors, located on the tank or fuel pump, for example, would operate to analyze the precombustion fuel, determining the mixture ratio. A second sensor, located on the fuel inlet, would operate to analyze the fuel during refueling of the vehicle, being intended to readily check for a possible fuel adulteration.

Figure 5:
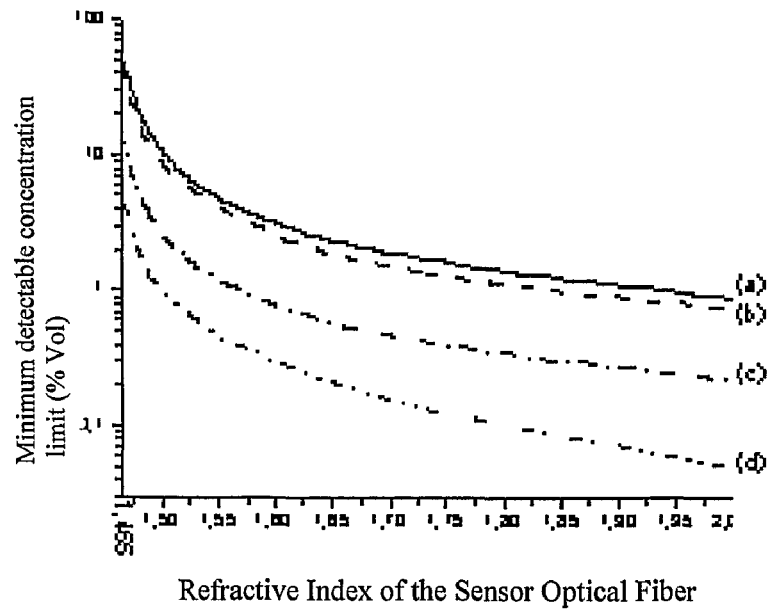
FIG. 5 shows the effect the refractive index of the sensor optical fiber has on the sensitivity of the optical system for mixtures of various compounds in diesel, wherein curve (a) represents a mixture of biodiesel in diesel, curve (b) represents a mixture of kerosene in diesel, curve (c) represents a mixture of gasoline in diesel, and curve (d) represents a mixture of ethanol in diesel.

In the case of fuel mixtures where one of the components makes up a small fraction in the mixture composition, or fuels having refractive indexes which are very near to each other, such as diesel and biodiesel, for example, the optical sensing becomes more difficult. Thus, it is proposed to optimize the sensing system according to the required detection accuracy by using special optical fibers whose refractive indexes are sufficiently higher than the refractive index of the mixture between these fuels, as shown in FIG. 5 of the drawings.

Figure 6:
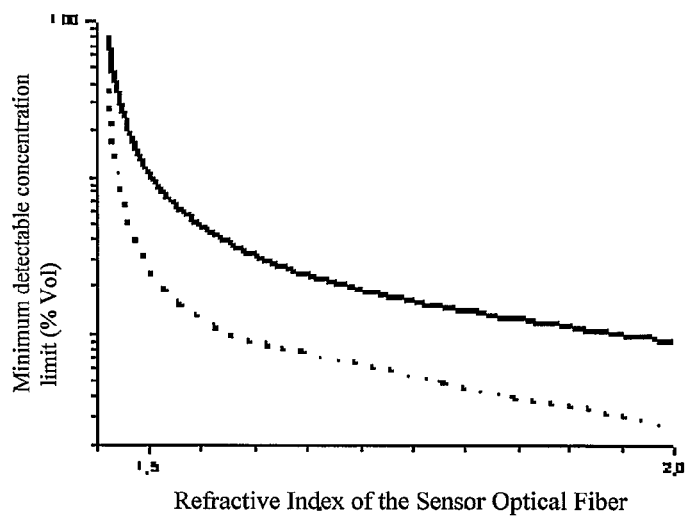
FIG. 6 shows an exemplary effect of the used light wavelength, λ=1550 nm (represented by the solid line curve) and λ=1310 nm (represented by the dashed line curve) on the reflectivity as a function of the refractive index variation of the liquid medium (biodiesel in diesel) into which the optical fiber is inserted.

The system proposed herein also shows a variation with respect to its detection sensitivity as a function of the wavelength used. Thus, the calibration of the system should take into account the wavelength of the light in order to avoid possible reading errors. The graph from FIG. 6 in the drawings shows an example of the effect the light wavelength has on reflectivity, in which an increase on the sensitivity of the sensor can be noted for some fuels, particularly in the case of biodiesel in diesel. This patent also contemplates a proper choice of the light wavelength to be used as an integral part of the process for optimizing the sensitivity and accuracy of the detection system.

The optical sensing method proposed herein also provides for correction of the effect the fuel temperature has on the refractive index, thus being clearly a thermally-compensated method. The refractive index variation of a liquid fuel is defined as a function of temperature through the temperature coefficient TC=dn/dT, specific to each type of fuel.

The correction of the effect of temperature on the refractive index of the fuel is carried out by simultaneously acquiring the temperature of the fuel being analyzed. With the processing unit having been supplied with refractive indexes of each fuel type at a previously-established standard temperature, as well as the respective temperature coefficients for these fuels, the correction of the refractive index into its equivalent at the standard temperature is carried out automatically, resulting in the proper identification of the analyzed fuel.

With respect to the fuel mixtures, their respective ratios are determined considering that the difference in the refractive index of the mixture, assigned to the temperature effect, is proportional to the average among all temperature coefficients of fuels making up the mixture, weighted by its respective volumetric ratios. With the processing unit having been supplied with refractive indexes of the fuels under analysis, as well as their respective temperature coefficients, the processing unit automatically computes refractive index values for each fuel making up the mixture into their equivalents at the measured temperature (T). The ratio of fuels $C_1$ and $C_2$ of a binary mixture can be determined from the following equation:

$$C_1 = \frac{n'_{mix} - n'_2}{n'_1 - n'_2}, \text{ with } C_1 + C_2 = 1$$

where $n_{mix}'$ corresponds to the refractive index of the binary mixture measured at a temperature T;

$n_1'$ and $n_2'$ correspond to refractive indexes of fuels 1 and 2, respectively, computed for the measured temperature T.

Figure 7:
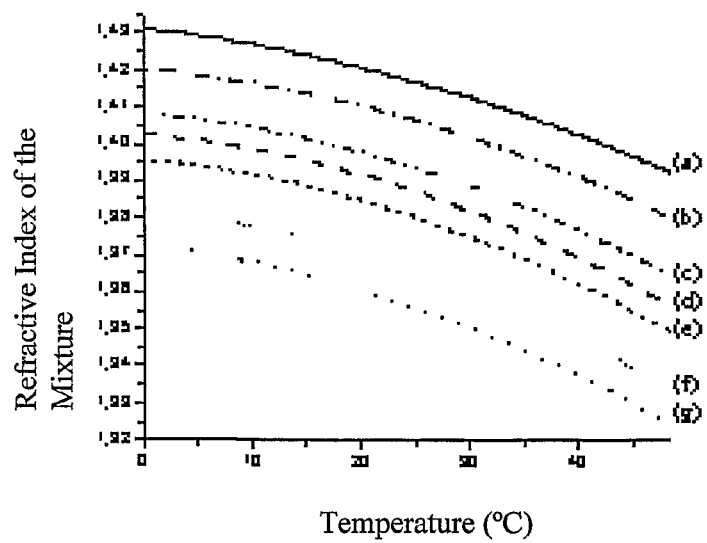
FIG. 7 shows the effect of temperature on the refractive index for different concentrations in the ethanol-gasoline mixture, wherein curve (a) represents pure gasoline, curve (b) represents 80% gasoline and 20% ethanol, curve (c) represents 60% gasoline and 40% ethanol, curve (d) represents 50% gasoline and 50% ethanol, curve (e) represents 40% gasoline and 60% ethanol, curve (f) represents 20% gasoline and 80% ethanol, and curve (g) represents pure ethanol.

Considering, as an example, the ethanol-gasoline mixture, the processing unit automatically corrects for refractive index values of ethanol and gasoline into their respective equivalents at the measured temperature, as shown in FIG. 7 of the drawings, allowing the ratio of the mixture to be determined according to the previously mentioned relationships.

The present invention also contemplates that the processing unit may be supplied with refractive indexes and temperature coefficients of any other liquids, particularly those found in fuel mixtures, such as, water, kerosene, solvents, vegetable oils, etc.

The invention claimed is:

1. An optical sensing system for liquid fuels, comprising:
   a light source,
   a splitter, whereby the splitter directs light from the light source for reference sensing and test probe sensing;
   detectors, whereby a detector measures a signal from the test probe sensing and a reference signal from the light source;
   a temperature sensor, whereby the temperature sensor provides temperature data;
   an optical fiber, and a storage and processing unit,
   wherein the optical fiber is used as a light guide and said system is used to determine the refractive indexes of liquid fuels through the principle of reflectivity, said system further identifying different types of liquid fuels and/or the ratio of fuels making up a mixture,
   and wherein the sensitivity of the system is determined by using optical fibers having refractive indexes higher than the refractive index of a liquid under measurement and the temperature data provides for correction of effect temperature of the fuel has on the refractive indexes.

2. Optical sensing system, according to claim 1, further comprising a data store storing values of refractive indexes of different types of liquid fuels at a predefined standard temperature, as well of other types of liquids feasible for adding to the fuels.

3. Optical sensing system, according to claim 1, wherein the system provides thermal compensation by simultaneously reading the temperature of the liquid fuel using the temperature sensor, obviating the effect of temperature variation on the refractive index.

4. Optical sensing system, according to claim 3, further comprising a data store storing values of refractive indexes of different types of liquid fuels at a predefined standard temperature and their respective temperature coefficients (TC), as well of any other types of liquids feasible for adding to the fuels.

5. Optical sensing system, according to claims 1 or 2, further comprising the optical fibers having a refractive index values in the range of 1.465 to 2.3.

6. Optical sensing system, according to claim 3, further comprising a cleaved-end optical fiber with or without polishing.

* * * * *